(12) United States Patent
Trost

(10) Patent No.: US 7,240,563 B2
(45) Date of Patent: Jul. 10, 2007

(54) METHOD FOR VERIFYING CONCRETE FLEXURAL STRENGTH

(76) Inventor: Steven Michael Trost, 2823 W. 28th Ave., Stillwater, OK (US) 74074

( * ) Notice: Subject to any disclaimer, the term of this patent is extended or adjusted under 35 U.S.C. 154(b) by 0 days.

(21) Appl. No.: 11/035,237

(22) Filed: Jan. 13, 2005

(65) Prior Publication Data
US 2005/0150306 A1    Jul. 14, 2005

Related U.S. Application Data

(60) Provisional application No. 60/535,834, filed on Jan. 13, 2004.

(51) Int. Cl.
*G01N 3/08* (2006.01)
(52) U.S. Cl. ...................................... 73/826
(58) Field of Classification Search ............ 73/784, 73/803, 78, 81, 84, 85, 826
See application file for complete search history.

(56) References Cited

U.S. PATENT DOCUMENTS

| | | | | |
|---|---|---|---|---|
| 3,673,861 A | * | 7/1972 | Handy | 73/841 |
| 3,841,595 A | * | 10/1974 | Brown | 249/14 |
| 5,222,957 A | * | 6/1993 | McColl et al. | 606/86 |
| 5,671,634 A | * | 9/1997 | Donovan | 73/150 A |
| 6,234,008 B1 | * | 5/2001 | Sjoblom et al. | 73/73 |

OTHER PUBLICATIONS

Oklahoma Transportation Authority, Special Provisions for Mix Design Procedures for Portland Cement Concrete Pavement, Jan. 2000, pp. 1-3, Oklahoma City, OK.
Oklahoma Transportation Authority, Addendum to Specification Section 414.04(q) Opening to Traffic, date unknown, pp. 1-6, Oklahoma City, OK.
Federal Aviation Administration, Engineering Brief No. 34A, "Referee Testing of Hardened Portland Cement Concrete Pavement—Percent Within Limits Revision", May 13, 2002, cover letter + pp. 1-4.

* cited by examiner

*Primary Examiner*—Max Noori

(57) ABSTRACT

The present invention relates to a method for verifying concrete flexural strength by establishing a predictive correlation between concrete flexural strength and a second strength parameter, such as direct tension or indirect tension, measuring the value of that second strength parameter for a batch of concrete, and estimating the flexural strength of the batch by way of the second strength value and the correlation.

22 Claims, 3 Drawing Sheets

MODIFIED PULLOUT INDIRECT TENSION

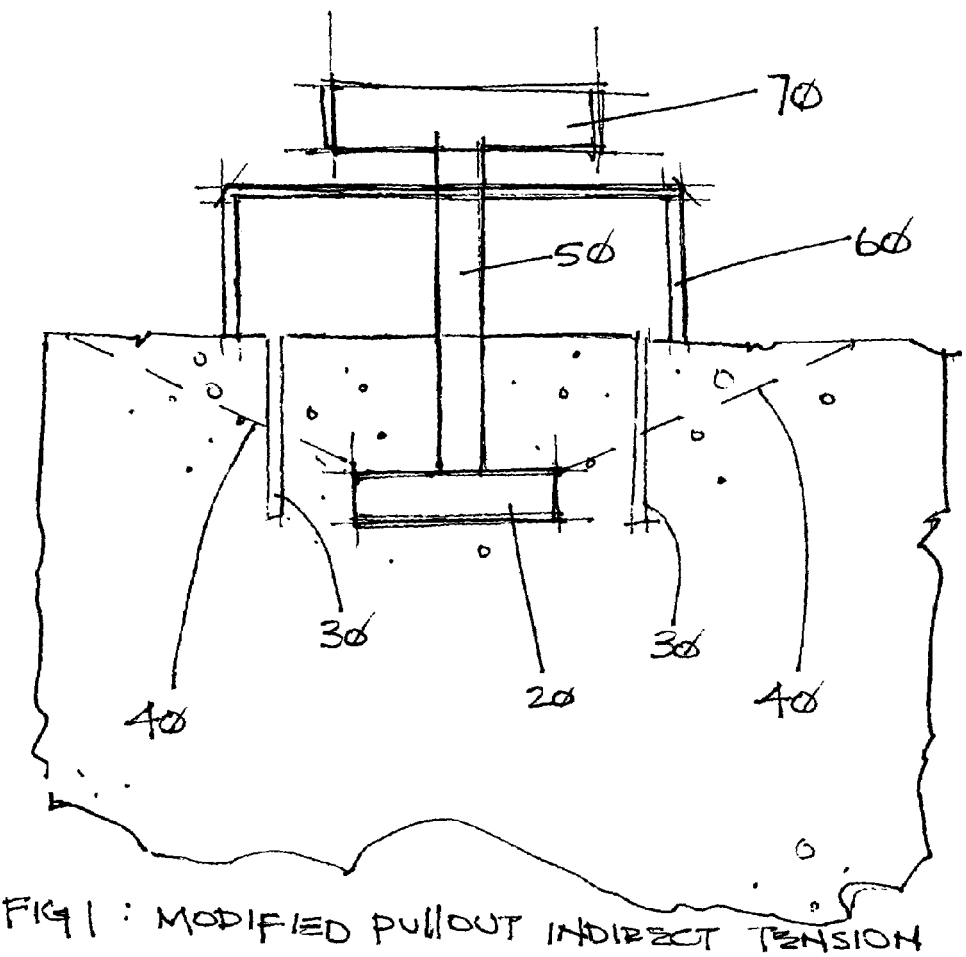
FIG 1: MODIFIED PULLOUT INDIRECT TENSION
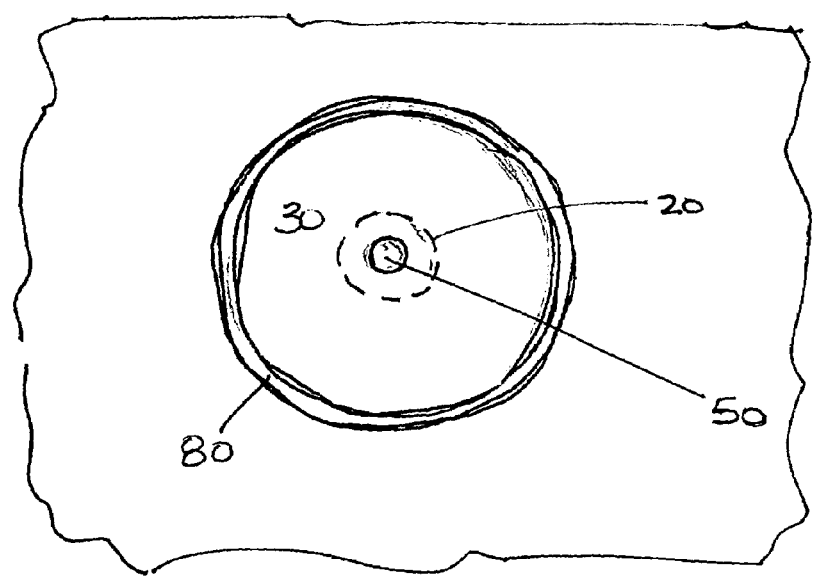
FIG 2: PARTIAL CORE AND EMBEDDED DISK

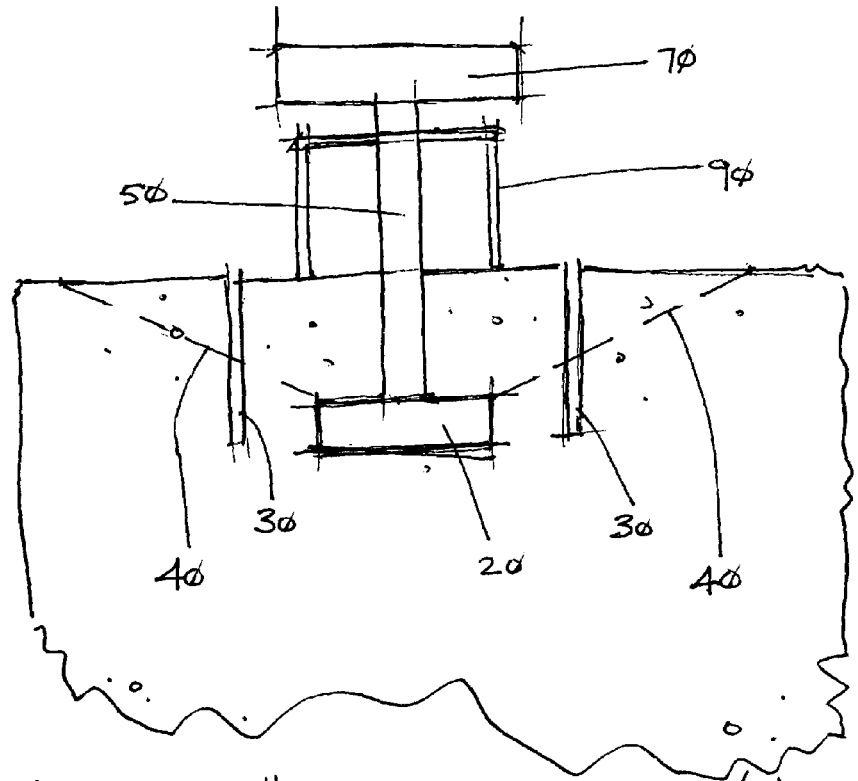
Fig 3: MODIFIED PULLOUT INDIRECT TENSION (ALT. SETUP)
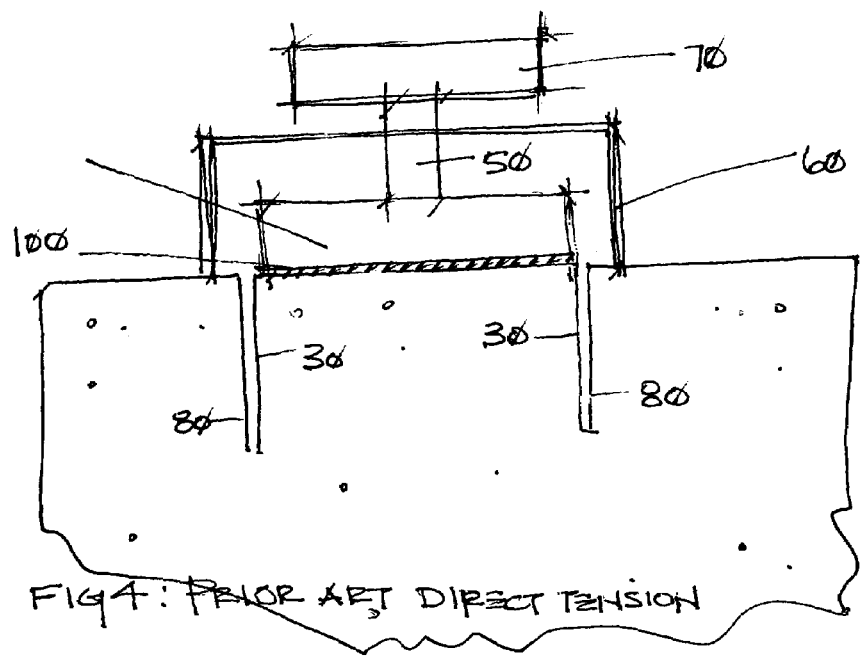
Fig 4: PRIOR ART DIRECT TENSION

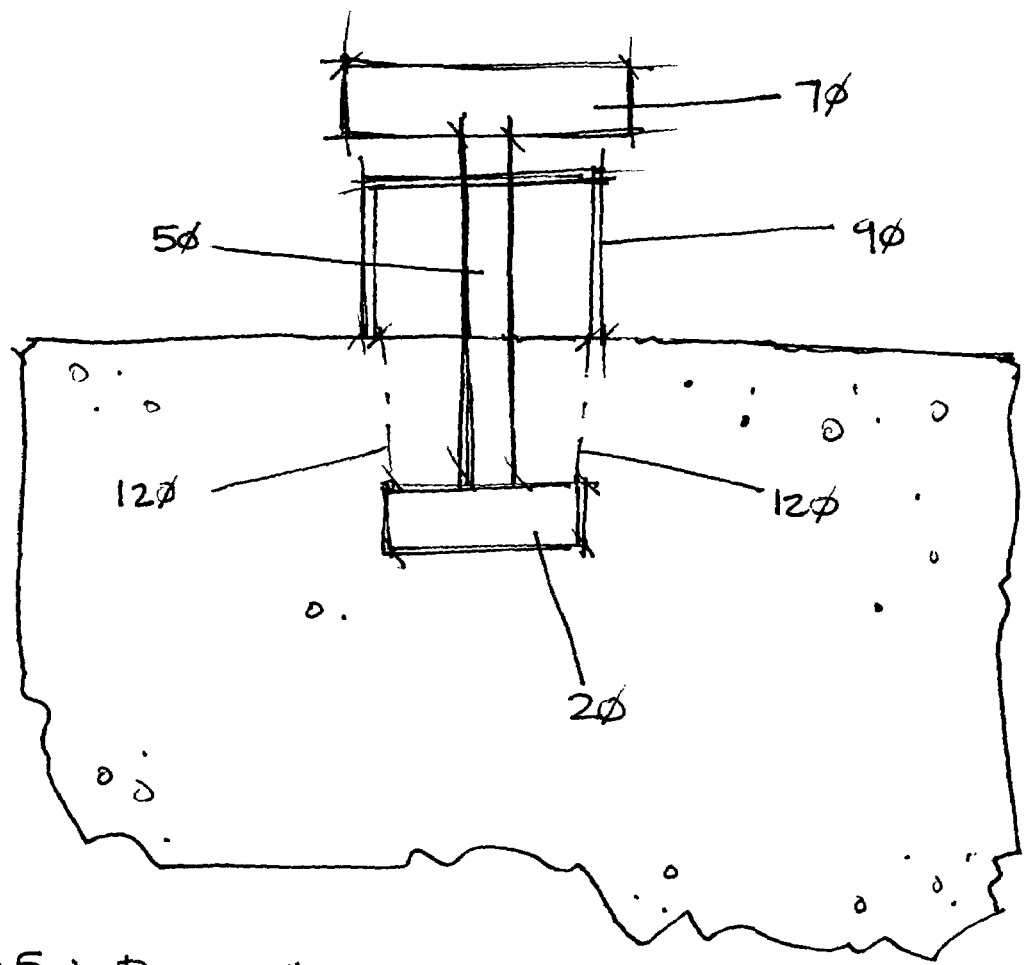
FIG 5: PRIOR ART PULLOUT TEST

METHOD FOR VERIFYING CONCRETE FLEXURAL STRENGTH

CROSS-REFERENCE TO RELATED APPLICATIONS

The present application claims priority to the following provisional patent application: METHOD FOR CONCRETE QUALITY CONTROL, filed on Jan. 13, 2004 and identified by U.S. Ser. No. 60/535,834. The entire content of the above-referenced patent application is hereby incorporated herein in its entirety.

The entire content of the research report entitled *Flexural Strength Quality Control for Concrete Pavements: Final Report*, dated June 2004, report number SS-0310302, is hereby incorporated by reference herein in its entirety.

STATEMENT REGARDING FEDERALLY SPONSORED RESEARCH AND DEVELOPMENT

Reduction-to-practice of portions of this invention was performed as part of a federally-sponsored research project.

BACKGROUND OF THE INVENTION

Concrete pavement design relies upon the flexural strength of the concrete as a primary design input. Concrete flexural strength is difficult to measure precisely due to the inherent problems associated with casting and handling the relatively large beam specimens required by the test procedure (e.g. according to ASTM C78). Because of this difficulty, many state highway agencies rely upon cylinder specimens tested in compression (e.g. according to ASTM C39) to control concrete quality in the field. However, the failure mechanisms and causes of failure can be considerably different between compressive-strength test methods and flexural-strength testing.

BRIEF SUMMARY OF THE INVENTION

By contrast, direct-tension measurements correlate quite well with flexural strengths. Direct-tension testing involves "pulling" a concrete specimen from opposite ends until the specimen breaks in two. Compressive-strength testing can overstate the strength of the concrete if flexural strength is the desired characteristic and if the concrete has characteristics that negatively affect flexural strength to a greater degree than they affect compressive strength. Poor paste-to-aggregate bond due to a coarse aggregate source with high fines content is an example. Direct-tension testing, on the other hand, represents failure mechanisms more similar to flexural strength testing and, as such, has the potential for providing a more robust measure of flexural strength whenever conventional beam testing is deemed infeasible or undesirable.

A preferred embodiment of the present invention involves a procedure for using direct-tension testing to verify flexural strength via direct tension measurements desirably coupled with conventional maturity testing.

BRIEF DESCRIPTION OF THE SEVERAL VIEWS OF THE DRAWING

FIG. 1 is a cross-sectional view of a "modified pullout" indirect tension measurement using an outer counterpressure ring.

FIG. 2 is a plan view of a partial core with an embedded object as prepared for a "modified pullout" indirect tension measurement.

FIG. 3 is a cross-sectional view of a "modified pullout" indirect tension measurement using an inner counterpressure ring.

FIG. 4 is a cross-sectional view of the prior art direct tension test.

FIG. 5 is a cross-sectional view of the prior art pullout test.

DETAILED DESCRIPTION OF THE INVENTION

One embodiment of the procedure could be implemented on a construction project as follows:

1. Perform conventional maturity calibration testing (versus flexural strength) with direct-tension testing (e.g. in accordance with ASTM C1583, using a device such as Germann Instruments' (Evanston, Ill.) BOND-TEST equipment) performed on additional beam, cube, or cylinder specimens or desirably using the "discarded" beam specimens (after they have been tested for flexural strength). This "calibration" procedure will produce three relationship curves (specific for the concrete mix to be used on the project): flexural strength versus maturity; direct-tension strength versus maturity; flexural strength versus direct-tension strength.
2. During concrete placement operations, periodically (e.g. three to six times per day) place a maturity sensor into the concrete pavement.
3. Periodically check the maturity sensors to determine when the pavement has presumably reached a desired flexural strength (e.g. 400 to 600 psi).
4. When the desired flexural strength has been presumably reached, perform direct-tension tests immediately adjacent to the maturity sensors.
5. Compare each measured direct-tension strength to the "predicted" direct-tension strength (based on the in-situ maturity reading in conjunction with the previously-established direct-tension-to-maturity relationship).
6. If the "actual" versus "predicted" strengths are close (e.g. within 10%), the concrete mix that was supplied to the project at that particular location is truly representative of the concrete mix approved for the project. As such, the flexural strength measurements (based on the maturity sensors) can be relied upon with confidence.
7. If the "actual" strengths are considerably less than the "predicted" strengths (e.g. more than 10% less), the concrete that was supplied to the project at that particular location is not the same as the concrete mix approved for the project. This provides a "red flag" to the inspection personnel that something has changed either with the raw materials supplied to the project, the batching process, or the proportions of raw materials.

This beneficial combination of in-situ direct-tension measurements with concrete maturity enables ongoing verification of the concrete supplied to the project without the need for any cylinder or beam specimens in the field! The can greatly reduce the human element from concrete-strength sampling and testing, particularly as it relates to measuring flexural strengths in the field.

Under the aforementioned embodiment, determination of the relationship between flexural and direct-tension strength is performed at the same time *and with the same test specimens* as the conventional flexural-strength-to-maturity relationship. This is possible because, as mentioned above, the direct-tension test can be easily performed on the "broken" beam specimens immediately after the flexural-strength maturity-calibration tests. This reuse of the maturity-calibration beam specimens assures even better correlations between direct-tension and flexural strength measurements since both tests can be performed on the exact same specimens.

Another embodiment of the procedure could be implemented on a construction project as follows:

1. Perform conventional maturity calibration testing (versus flexural strength) with direct-tension testing (using a device such as German Instruments' (Evanston, Ill.) BOND-TEST equipment) performed on additional beam, cube, or cylinder specimens or desirably using the "discarded" beam specimens (after they have been tested for flexural strength).
2. During concrete placement operations, periodically (e.g. There to six times per day) cast test specimens and place a maturity sensor in at least one of the specimens each time specimens are cast. One or more maturity sensors can also be placed into the structure.
3. Periodically check the maturity sensor(s) to determine when a desired flexural strength has been achieved.
4. Perform direct-tension tests on the cast specimens.
5. Compare each measured direct-tension strength to the "predicted" direct-tension strength (based on the maturity reading in conjunction with the previously-established direct-tension-to-maturity relationship).
6. If the "actual" versus "predicted" strengths are close (e.g. within 10%), the concrete mix that was supplied to the project at that particular location is truly representative of the concrete mix approved for the project. As such, the flexural strength measurements (based on maturity sensors placed in the field) can be relied upon with confidence.
7. If the "actual" strengths are considerably less than the "predicted" strengths (e.g. more than 10% less), the concrete that was supplied to the project at that particular location is not the same as the concrete mix approved for the project. This provides a "red flag" to the inspection personnel that something has changed either with the raw materials supplied to the project, the batching process, or the proportions of raw materials.

The above embodiment requires specimens to be cast in the field. However, those specimens can desirably be cast as cylinder specimens (which are easy to cast and relatively lightweight) rather than beam specimens (which are more difficult to cast, more difficult to transport, heavier, and more easily damaged).

Whereas a strength-gradient can exist from the inside out in a concrete specimen or even within a concrete structure (due to the increased rate of hydration that typically takes place within a concrete mass due to higher internal temperatures), obtaining repeatable and reproducible direct tension test results may at times be more desirably achieved by cutting beam or cylinder specimens (or cylindrical core specimens extracted from the structure if the structure itself is to be tested) transversely in half (or in thirds), then performing the direct tension tests on the cut faces of the specimens.

In addition to simple direct-tension testing, indirect measures of tensile strength can be performed as a part of the "maturity calibration" using commercially-available embedment and pullout equipment such as Germann Instruments' (Evanston, Ill.) "LOK-TEST" embedded inserts (e.g. in accordance with ASTM C900). The user can determine the tensile strength of the concrete indirectly by recording the load at which the occurrence of the "first-fracture-surface" occurs as the embedded insert is being pulled. The "second-fracture-surface" of the standard embedment and pullout test has been shown to be extremely well correlated with the compressive strength of the concrete (ASTM C900). The "first-fracture-surface" can be correlated with the direct-tension measurements (and, hence, with the flexural strength measurements as well). Both fracture surfaces are typically produced during the standard embedment and pullout test procedure. The identification of the timing and associated maximum load at the occurrence of the first fracture surface can be determined acoustically by using an acoustical sensor, such as microDISP by Physical Acoustics Corporation (Princeton Jct, N.J.), during the standard pullout test by simply "listening" for the distinct acoustic signals generated by the first major crack. After the occurrence of the first-fracture-surface has been identified, the standard pullout test can be completed, thus providing both a tensile strength and a compressive strength measure from a single embedment and pullout test.

An alternative indirect-tensile test procedure is depicted in FIGS. 1, 2, and 3 which involves conducting a "modified pullout" test wherein the concrete 10 is cored around the embedded object 20 such that when the "first-fracture-surface" 40 occurs, the fracture surface intersects the walls of the partial core 30 thus eliminating the accumulation of any load resistance beyond the "first-fracture-surface" 40, effectively causing a plateau, dip, or complete cessation with respect to the load-carrying capacity of the partial core 30. An outer counterpressure ring 60 spans the partial core 30 and the annular space 80 which surrounds the partial core 40. A pull machine 70 pulls upward on a pull bolt 50 which is coupled to the embedded object 20, thus transferring the force from the pull machine 70 to the embedded object 20. FIG. 2 shows the embedded object 20 centered in the partial core 30. FIG. 3 shows the same cross-section as FIG. 1 except an inner counterpressure ring 90 is used. FIG. 4 shows a cross-sectional view of the prior art direct tension test setup with a metal disk 110 adhered to the partial core 30 with an adhesive 100. FIG. 5 shows a cross-sectional view of the prior art pullout test with the embedded object 20 with the smaller counterpressure ring 90 and the second fracture surface 120.

To achieve the intersection between the first-fracture-surface and the walls of the partial core, the partial core must extend beyond the conical zone of the first-fracture-surface, which will normally require the core to extend beyond about 50%, desirably to about 100%, of the embedment depth of the embedded object. With this modified pullout test, the remainder of the standard pullout test results (i.e. to determine compressive-strength) cannot be obtained unless the core is constrained after the occurrence of the "first-fracture-surface". The occurrence of the "first-fracture-surface" can be identified by a flattening out and/or dip in the load-versus-time curve (i.e. the load applied by the pullmachine stops increasing and/or begins to decrease with additional strain). At this point, the outer wall of the core can be constrained, such as with steel bands, allowing the standard pullout test to be completed, thus also providing both a tensile strength and compressive strength measure from the test. However, if tensile strength is the only desired characteristic, the modified pullout test can be stopped after the plateau or dip is observed in the load-time curve.

The aforementioned modified pullout procedure can also be performed using non-standard shapes for the embedment object (in lieu of the disk specified in ASTM C900). A number of different shapes can be meaningfully utilized, such as a disk, sphere, ellipsoid, torroid, ring, rectangular prism, and so forth. In addition, the aforementioned shapes can be meaningful utilized in various orientations and rotations.

As detailed within this specification, the present invention provides significant advantages over current methods for determining the flexural strength of concrete pavements. Furthermore, the invention and its benefits (i.e. ongoing verification of the concrete supplied to the project without need for casting beam specimens in the field) can be readily and easily transferred to other types of concrete construction (i.e. where compressive strengths, rather than flexural strengths, are of primary interest) and other types of materials testing. By way of example, for instance, by using the LOK-TEST "second-fracture-surface" compressive-strength measurements in lieu of direct-tension tests. As such, a preferred embodiment of the present invention comprises an effective means for providing expeditious and reliable verification of concrete strengths during construction without the need for casting concrete beams in the field.

In addition, the present invention can be readily applied to many aspects of materials testing beyond the concrete materials examples detailed herein. For instance, aspects of the present invention can be used to verify the quality of materials such as steel and other metals, ceramics, fiber-reinforced composites, other composite materials, and so forth.

From the above description it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims. Changes may be made in the embodiments of the invention described herein, or in the parts or the elements of the embodiments described herein or in the step or sequence of steps of the methods described herein, without departing from the spirit and/or the scope of the invention.

REFERENCES

ASTM C39-01. (2003). "Standard Test Method for Compressive Strength of Cylindrical Concrete Specimens." 2003 *ASTM Standards Vol.* 04.02. West Conshohocken, Pa.: ASTM International.

ASTM C78-02. (2003). "Standard Test Method for Flexural Strength of Concrete (Using Simple Beam with Third-Point Loading)." 2003 *ASTM Standards Vol.* 04.02. West Conshohocken, Pa.: ASTM International.

ASTM C900-01. (2003). "Standard Test Method for Pullout Strength of Hardened Concrete" 2003 *ASTM Standards Vol.* 04.02. West Conshohocken, Pa.: ASTM International.

ASTM C1583-04. (2005). "Standard Test Method for Pullout Strength of Hardened Concrete" 2005 *ASTM Standards Vol.* 04.02. West Conshohocken, Pa.: ASTM International.

I claim:

1. A method for verifying concrete flexural strength comprising
   physically testing a concrete sample to obtain flexural strength,
   establishing a predictive correlation between concrete flexural strength and a second strength parameter,
   measuring the value of said second strength parameter for a batch of concrete,
   establishing a strength-maturity correlation for flexural strength, and
   estimating the flexural strength of said batch by way of said second strength value and said maturity correlation.

2. A method for verifying concrete flexural strength comprising
   physically testing a concrete sample to obtain a flexural strength,
   establishing a predictive correlation between concrete flexural strength and a second strength parameter,
   measuring the value of said second strength parameter for a batch of concrete,
   establishing a strength-maturity correlation for one or more strength parameters, and
   estimating the flexural strength of said batch by way of said second strength value and said predictive correlation.

3. The method of claim 2 further comprising
   comparing said maturity correlation to an actual measurement of said second strength parameter.

4. The method of claim 2 wherein said second strength parameter comprises tensile strength measured by direct tension.

5. The method of claim 2 wherein said second strength parameter comprises tensile strength measured by an indirect tension method.

6. A method for verifying concrete flexural strength comprising
   physically testing a concrete sample to obtain flexural strength,
   establishing a predictive correlation between concrete flexural strength and a second strength parameter,
   measuring the value of said second strength parameter for a batch of concrete, and
   estimating the flexural strength of said batch by way of said second strength value and said correlation, wherein said second strength parameter comprises tensile strength measured by an indirect tension method and wherein said indirect tension method comprises sensing the occurrence of a first fracture surface.

7. A method for verifying concrete flexural strength comprising
   establishing a predictive correlation between concrete flexural strength and a second strength parameter,
   measuring the value of said second strength parameter for a batch of concrete, and
   estimating the flexural strength of said batch by way of said second strength value and said correlation, wherein said second strength parameter comprises tensile strength measured by an indirect tension method and wherein said indirect tension method comprises embedding an object in the concrete,
   circumscribing said object with a partial core that extends to at least half the embedment depth of said object, and
   pulling against said object until said partial core fractures.

8. The method of claim 2 wherein said one or more strength parameters comprises flexural strength.

9. The method of claim 2 wherein said one or more strength parameters comprises tensile strength.

10. The method of claim 9 wherein said tensile strength is measured by direct tension.

11. The method of claim 9 wherein said tensile strength is measured by an indirect tension method.

12. The method of claim 11 wherein said indirect tension method comprises
  embedding an object in the concrete,
  circumscribing said object with a partial core that extends to at least half the embedment depth of said object, and
  pulling against said object until said partial core fractures.

13. The method of claim 11 wherein said indirect tension method comprises sensing the occurrence of a first fracture surface.

14. The method of claim 13 wherein the occurrence of said first fracture surface is determined acoustically.

15. The method of claim 6 wherein the occurrence of said first fracture surface is determined acoustically.

16. The method of claim 5 wherein said indirect tension method comprises sensing the occurrence of a first fracture surface.

17. The method of claim 16 wherein the occurrence of said first fracture surface is determined acoustically.

18. The method of claim 5 wherein said indirect tension method comprises
  embedding an object in the concrete,
  circumscribing said object with a partial core that extends to at least half the embedment depth of said object, and
  pulling against said object until said partial core fractures.

19. The method of claim 1 wherein one or more test values for said second strength parameter is measured using a concrete specimen also used to measure concrete flexural strength.

20. The method of claim 2 wherein one or more test values for said second strength parameter is measured using a concrete specimen also used to measure concrete flexural strength.

21. The method of claim 6 wherein one or more test values for
  said second strength parameter is measured using a concrete specimen also used to measure
  concrete flexural strength.

22. The method of claim 7 wherein one or more test values for
  said second strength parameter is measured using a concrete specimen also used to measure
  concrete flexural strength.

* * * * *